US008318927B2

(12) United States Patent
Lundbeck et al.

(10) Patent No.: US 8,318,927 B2
(45) Date of Patent: Nov. 27, 2012

(54) 6-(4-CYCLOPROPYLPIPERAZIN-1-YL)-2'-METHYL-[3, 4']-BIPYRIDINE AND ITS USES AS A MEDICAMENT

(75) Inventors: Jane Marie Lundbeck, Glostrup (DK); Rolf Hohlweg, Humblebaek (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 429 days.

(21) Appl. No.: 12/301,919

(22) PCT Filed: May 21, 2007

(86) PCT No.: PCT/EP2007/054849
§ 371 (c)(1),
(2), (4) Date: Nov. 21, 2008

(87) PCT Pub. No.: WO2007/135111
PCT Pub. Date: Nov. 29, 2007

(65) Prior Publication Data
US 2011/0071159 A1  Mar. 24, 2011

(30) Foreign Application Priority Data

May 23, 2006  (EP) .................................. 06114398

(51) Int. Cl.
*C07D 223/00* (2006.01)
(52) U.S. Cl. ......................... 540/1; 514/253.01; 544/364
(58) Field of Classification Search ............. 514/253.01; 544/364
See application file for complete search history.

(56) References Cited

U.S. PATENT DOCUMENTS

| | | | |
|---|---|---|---|
| 2,993,899 A | 7/1961 | Dawson | |
| 3,309,370 A | 3/1967 | Schut | |
| 3,886,161 A | 5/1975 | Hardtmann | |
| 4,223,036 A | 9/1980 | Heeres et al. | |
| 4,251,658 A | 2/1981 | Szilagyi et al. | |
| 4,265,894 A | 5/1981 | Gootjes | |
| 4,616,014 A | 10/1986 | Teraji et al. | |
| 4,673,675 A | 6/1987 | Robba et al. | |
| 5,670,505 A | 9/1997 | Matsuo et al. | |
| 6,316,475 B1 | 11/2001 | Bennani et al. | |
| 7,294,626 B2 | 11/2007 | Hohlweg | |
| 2003/0073672 A1 | 4/2003 | Breitenbucher et al. | |
| 2003/0236259 A1 | 12/2003 | Hohlweg et al. | |
| 2004/0023946 A1 | 2/2004 | Peschke et al. | |
| 2005/0028438 A1 | 2/2005 | Campana | |
| 2009/0111808 A1* | 4/2009 | Bertrand et al. | 514/235.5 |
| 2009/0176793 A1 | 7/2009 | Hohlweg | |
| 2009/0264435 A1 | 10/2009 | Hohlweg et al. | |
| 2009/0312309 A1 | 12/2009 | Hohlweg et al. | |
| 2010/0267721 A1 | 10/2010 | Hohlweg et al. | |
| 2010/0298316 A1 | 11/2010 | Dorwald et al. | |
| 2011/0071159 A1 | 3/2011 | Lundbeck et al. | |

FOREIGN PATENT DOCUMENTS

| | | |
|---|---|---|
| AU | 639529 | 5/1991 |
| DE | 2609746 | 10/1976 |
| DE | 2804096 | 8/1978 |
| DE | 2824764 | 12/1979 |
| DE | 3803860 | 8/1989 |
| EP | 0 177 392 | 4/1986 |
| EP | 0 200 024 | 11/1986 |
| EP | 0 236 140 | 9/1987 |
| EP | 0 327 912 | 4/1992 |
| EP | 0 385 237 | 6/1994 |
| EP | 0459819 B1 | 8/1996 |
| EP | 0978512 A1 | 2/2000 |
| EP | 1 020 445 | 7/2000 |
| GB | 753166 | 7/1956 |
| GB | 1 345 880 | 2/1974 |
| WO | WO 97-02245 | 1/1997 |
| WO | WO 98-27081 | 6/1998 |
| WO | WO 99-21845 | 5/1999 |
| WO | WO 00-66578 | 11/2000 |
| WO | WO 01-44201 | 6/2001 |
| WO | WO 01-64545 | 9/2001 |
| WO | WO 01-64645 | 9/2001 |
| WO | WO 01-66534 | 9/2001 |
| WO | WO 01-74810 | 10/2001 |
| WO | WO 03-066604 | 8/2003 |
| WO | WO 2004-054973 | 7/2004 |
| WO | WO 2005-009976 | 2/2005 |
| WO | WO 2006-058649 | 6/2006 |

OTHER PUBLICATIONS

Ballaben et al., "Reactivity of cyclopentanoone enamines towards non-symmetric electrophillic diazenes," Gazetta Chimica Italiana, vol. 123, No. 7, pp. 387-391 (1993) (abstract only).
Hancock, "The Challenge of Drug Discovery of a GPCR Target: Analysis of Preclinical Pharmacology of Histamine H3 Antogonists/Inverse Agonists," Biochemical Pharmacology, vol. 71, pp. 1103-1113 (2006).
Hori et al., "Novel 4-substituted 2-piperazinylquinazolines as potent anticonvulsive and antihypoxic agents," Chemical & Pharmaceutical, vol. 38, pp. 1286-1291 (1990) (abstract only).
Hori et al., "Potential nootropic agents, 4-alkoxy-2-(1-piperazinyl) quinazoline derivatives," Chemical & Pharmaceutical Bulletin, vol. 39, pp. 367-371 (1991) (abstract only).
Leurs et al., "The Histamina H3 Receptor: from Gene Cloning to H3 Receptor Drugs," Nature Reviews/Drug Discovery, vol. 4, pp. 107-120 (2005).
Leurs et al., "The Medicinal Chemistry and Therapeutic Potentials of Ligands of the Histamine H3 Receptor," Progress in Drug Research, vol. 45, pp. 107-165 (1995).
Leurs et al., "Therapeutic Potential of Histamine H3 Receptor Agonists and Antagonists," Trends in Pharmacological Sciences, vol. 19, No. 5, pp. 177-183 (1998).
Mackins et al., "Therapeutic Potential of H3-receptor Agonists in Myocardial Infarction," Expert Opinion on Investigational Drugs, vol. 9, No. 11, pp. 2537-2542 (2000).
Malmlof et al., "Targeting of the Central Histaminergic System for Treatment of Obesity and Associated Metabolic Disorders," Drug Development Research, vol. 67, pp. 651-665 (2006).

(Continued)

*Primary Examiner* — Brandon Fetterof
*Assistant Examiner* — Jean Cornet
(74) *Attorney, Agent, or Firm* — Samuel B. Rollins

(57) ABSTRACT

6-(4-Cyclopropylpiperazin-1-yl)-2'-methyl-[3,4']bipyridinyl and salts and hydrates thereof interact with the histamine H3 receptor are defined.

10 Claims, No Drawings

OTHER PUBLICATIONS

Mazarguil et al., "Examines of N-methyl- and N-phanylpiperazine. I. Synthesis and physicochemical study." Bulletin de la Societe Chimique de France, vol. 1, pp. 319-324 (1969) (abstract only).

Mazarguil et al., "Enamines of N-methyl and N-phenylpiperazines. Synthesis, of unsymmetrical N,N'-disubstituted and N-monosubstituted piperazines," Sciences Chimique, vol. 267, pp. 724-727 (1968) (abstract only).

McLeod et al., "Sch 50971, an Orally Active Histamine H3 Receptor Agonist, Inhibits Central Neurogenic Vascular Inflammation and Produces Sedation in the Guinea Pig." J. Pharmacol. Exp. Ther., vol. 287, pp. 43-50 (1998).

Morisset et al., "High Constitutive Activity of Native H3 Receptors Regulates Histamine Neurons in Brain," Nature, vol. 408, pp. 860-864 (2000).

Stark et al., "Developments of Histamine H3-Receptor Antagonists," Drugs of the Future, vol. 21, No. 5, pp. 507-520 (1996).

Tozer at al., "Histamine H3 Receptor Antagonists," Expert Opinion on Therapeutic Patents, vol. 10, No. 7, pp. 1045-1055 (2000).

Wu et al., "Synthesis and platelet aggregation activity of 6-[4-(substituted-piperazinyl)phenyl]-4,5-dihydro-3(2H)-pyridazinones," Zhongguo Yaowu Huaxue Zazhi, vol. 9, pp. 172-175, 185 (1999) (abstract only).

Abdel-Magid et al., "Reductive Amination of Aldehydes and Ketones with Sodium . . ." J. Org. Chem., vol. 61, pp. 3849-3862, (1996).

Adam et al., "Concise synthesis of 1H-pyrazin-2-ones and 2-aminopyrazines" Synlett, No. 11, pp. 2031-2033, (2004).

Ballaben et al., "Reactivity of cyclopentanone enamines towards non-symmetric electrophilic diazenes.", Gazette Chimica Italiana, vol. 123, pp. 387-391, (1993).

Brown et al., "Unfusd Heterbicycles as Amplifiers of Phleomycin . . ." Australian Journal of Chemistry, vol. 34, pp. 2423-2429, (1981).

Celanire et al., Keynote review: Histamine H3 receptor antagonists reach out for the clinic DDT—Drug Discovery Today, Elsevier Science Ltd, GB, vol. 10, No. 23-24, Dec. 2005, pp. 1613-1627.

Contreras et al., "Aminopyridazines as acetylcholinesterase inhibitors" J. Med. Chem., vol. 42, pp. 730-741, (1999).

Contreras et al., "Design, synthesis, and stucture-activity relationships of a series of . . ." J. Med. Chem., vol. 44, pp. 2707-2718, (2001).

Coppola et al., "Pyrimidones 2. Synthesis and Reactions of 2 Chloro Pyrimidines" J. Heterocyclic Chemistry, vol. 17, pp. 1479-1482, (1980).

Database Beilstein, XP002355793 abstract, 1991.
Database Beilstein, XP002355794 abstract, 1988.
Database Beilstein, XP002355795 abstract, 1991.
Database Beilstein, XP002355796 abstract, 1989.

Giannangeli et al., J. Med. Chem., vol. 42, pp. 336-345, (1999).

Haugwitz et al., "Antiparasitic agents. 5. Synthesis and anthelmintic activities of novel . . ." J. Med. Chem., vol. 25, pp. 969-974, (1982).

Hori et al., "Nove 4-substituted 2-piperazinylquinazolines as potent anticonvulsive and antihypoxic agents." Chemical & Pharmaceutical Bulletin, vol. 38, pp. 1286-1291, (1990).

Hori et al., "Potential nootropic agents, 4-alkoxy-2-(1-piperazinyl) quinazoline derivatives." Chemical & Pharmaceutical Bulletin, vol. 39, pp. 367-37, (1991).

International Search Report for related PCT application, PCT/DK03/00071, mailed Jul. 29, 2003.

International Search Report for related PCT application, PCT/EP2006/063753, mailed Apr. 27, 2007.

International Search Report for related PCT application, PCT/EP2007/054849, mailed Sep. 3, 2007.

International Search Report for related PCT application, PCT/EP2007/054940, mailed Oct. 25, 2007.

International Search Report for related PCT application, PCT/US08/64106, mailed Aug. 15, 2008.

Kawaguchi et al., "Parallel dose-response studies of the voltage-dependent . . ." European Journal of Pharmacology, vol. 364, pp. 99-105, (1999).

Klauschenz et al., "Synthesis and cardiotonic activity of 6-substituted 5-cyano-(3,4'-bipyridine) . . ." European J. Med. Chem., vol. 29, pp. 175-184, (1994).

Levay et al., "Correlation of the Chemical Reactivity of Some Tetrazine Derivatives with their Reactivity towards . . ." Journal of Physical Chemistry, vol. 108, pp. 1753-1756, (2004).

Linney et al., J. Med. Chem., vol. 43, pp. 2362-2370, (2000).

Lumma et al., "Piperazinylpyrazines with central serotoninmimetic activity" J. Med. Chem., vol. 21, pp. 536-542, (1978).

Mazarguil et al., "Enamines of N-methyl- and N-phenylpiperazines. Synthesis of unsymmetical . . ."Sciences Chimique, vol. 267, pp. 724-727, (1968).

Mazarguil et al., "Enamines of N-methyl-and N-phenylpiperazine. I. Synthesis and physicochemical study." Bulletin De La Societe Chimique De France, vol. 1, pp. 319-324, (1969).

Mokrosz et al., J. Med. Chem., vol. 35, pp. 2369-2374, (1992).

Parrot et al., "Synthesis of Substituted 3-amino-6-arylpyridazines via suzuki Reaction" Synthesis, No. 7, pp. 1163-1168, (1999).

Prasad et al., J. Med. Chem., vol. 11, pp. 1144-1150, (1968).

Rival et al., "5-HT3 Antagonists Derived from Aminopyridazine-type Musbarinic M1 Agonists" J. Med. Chem., vol. 41, pp. 311-317, (1998).

Steck et al., "Pyridazines Part 8 Some 6 Aryl-3 Basically Substituted Pyridazines" J. of Heterocyclic Chemistry, vol. 12, pp. 1009-1013, (1975).

Tafesse et al., "Synthesis and evaluation of pyridazinylpiperazines as vanilloid receptor 1 antagonists" Bioorganic & Medicinal Chemistry Letters, vol. 14, pp. 5513-5519, (2004).

Werbel et al., "Synthesis and Antimalarial Effects of N N DI Alkyl-6 (Substituted Phenyl) . . ." J. of Heterocyclic Chemistry, vol. 16, pp. 881-894, (1979).

Wu et al., "Synthesis and platelet aggregation activity of 6-[4-substituted-piperazinyl)phenyl]-4,5-dihydro-3(2H)-pyridazinones." vol. 9, pp. 172-175 (1999).

Hancock, "The Challenge of Drug Discovery of a GPCR Target: Analysis of Preclinical Pharmacology of Histamine H3 Antagonists/Inverse Agonists," Biochemical Pharmacology, vol. 71, pp. 1103-1113 (2006).

* cited by examiner

6-(4-CYCLOPROPYLPIPERAZIN-1-YL)-2'-METHYL-[3, 4']-BIPYRIDINE AND ITS USES AS A MEDICAMENT

CROSS-REFERENCE TO RELATED APPLICATIONS

This application is the United States national stage application, pursuant to 35 U.S.C. 371, of PCT/EP2007/054849, filed May 21, 2007 which claims benefit of European Patent Application No. 06114398.8, filed May 23, 2006.

FIELD OF THIS INVENTION

The present invention relates to novel compounds, to the use of these compounds in pharmaceutical compositions, to pharmaceutical compositions comprising the compounds, and to methods of treatment employing these compounds or compositions. The compounds of this invention show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

BACKGROUND OF THIS INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e., it is active in the absence of an agonist). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

In view of the art's interest in histamine H3 receptor agonists, inverse agonists and antagonists, novel compounds which interact with the histamine H3 receptor would be a highly desirable contribution to the art. Several publications disclose the preparation and use of histamine H3 agonists and antagonists. Most of these are imidazole derivatives. However, recently some imidazole-free ligands of the histamine H3 receptor have been described. For example, WO 03/066604 (Novo Nordisk A/S) relates to aryl- and heteroarylpiperazines.

OBJECTS OF THIS INVENTION

One object of this invention is to furnish compounds having a reducing effect on the intake of food.

A further object of this invention is to furnish compounds which can be used for the reduction of weight.

A further object of this invention is to furnish compounds which can be used for the treatment of overweight or obesity.

A further object of this invention is to furnish compounds which can be used for the suppression of appetite or for satiety induction.

A further object of this invention is to furnish compounds which can be used for the treatment of type 2 diabetes.

A further object of this invention is to furnish compounds which can be used to cure or prevent other of the diseases or pharmacological conditions mentioned below.

A further object of this invention is to furnish compounds which fulfils the general requirements to a medicament, such as non-toxicity, non-mutageneity and other common criteria to a medicament.

Further objects of this invention are to provide compounds having a low inhibition of the hERG potassium channel.

A further object of this invention is to overcome or ameliorate at lest some of the disadvantages of the prior art.

Not each and every of the objects mentioned may be fully overcome or ameliorated.

DEFINITIONS

The term "the compounds of this invention" covers the compound claimed herein and it covers the compound of formula I and any salt or solvate thereof.

The term "solvate" as used herein is a complex of defined stoichiometry formed by a solute (in casu, a compound according to the present invention) and a solvent. Solvents are those commonly used in the pharmaceutical art, by way of example, water, ethanol, acetic acid, and the like. The term "hydrate" refers to the complex where the solvent molecule is water.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "biohydrolyzable ester" as used herein is an ester of a drug substance (in this invention, a compound of formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (for example, $C_{1-4}$), lower acyloxyalkyl esters, lower alkoxyacyloxyalkyl esters, alkoxyacyloxy esters, alkyl acylamino alkyl esters, and choline esters.

The term "biohydrolyzable amide" as used herein is an amide of a drug substance (in this invention, a compound of general formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "metabolite" as used herein is any intermediate or product resulting from metabolism.

The term "metabolism" as used herein refer to the biotransformation of a drug substance (in this invention, a compound of general formula I) administered to a patient.

The representative examples mentioned above are specific embodiments of this invention.

SUMMARY OF THIS INVENTION

The invention relates to the compound of formula I specified below and salts and hydrates thereof. The compounds of this invention differ structurally from the known compounds.

The invention also relates to the use of said compounds in therapy, and in particular to pharmaceutical compositions comprising said compounds.

In another embodiment, the invention relates to methods of treatment, the method comprising administering to a subject in need thereof an effective amount of one or more compounds according to formula I.

In a still further embodiment, the invention relates to the use of compounds according to formula I in the manufacture of medicaments.

DETAILED DESCRIPTION OF THIS INVENTION

Due to their interaction with the histamine H3 receptor, the compounds of this invention as defined in the claims below and elsewhere in this specification are useful in the treatment of a wide range of conditions and disorders in which an interaction with the histamine H3 receptor is beneficial. Thus, the compounds may find use, for example, in the treatment of diseases of the central nervous system, the peripheral nervous system, the cardiovascular system, the pulmonary system, the gastrointestinal system and the endocrinological system.

The compounds of this invention interact with the histamine H3 receptor and are accordingly particularly useful in the treatment of a variety of diseases or conditions in which histamine H3 interactions are beneficial.

In one aspect, the invention provides the use of a compound according to formula I in a pharmaceutical composition. The pharmaceutical composition may in another aspect of the invention comprise, as an active ingredient, at least one compound according to formula I together with one or more pharmaceutically acceptable carriers or excipients. In another aspect, the invention provides such a pharmaceutical composition in unit dosage form, comprising from about 0.05 mg to about 1000 mg, for example, from about 0.1 mg to about 500 mg, such as from about 0.5 mg to about 200 mg, of the compound according to formula I.

In another aspect, the invention provides the use of a compound of this invention for the preparation of a pharmaceutical composition for the treatment of diseases and disorders in which an inhibition of the H3 histamine receptor has a beneficial effect.

In another aspect, the invention provides the use of a compound of this invention for the preparation of a pharmaceutical composition having histamine H3 antagonistic activity or histamine H3 inverse agonistic activity.

In another aspect the invention provides the use of a compound of this invention for the preparation of a pharmaceutical composition for the reduction of weight.

In another aspect, the invention provides the use of a compound of this invention for the preparation of a pharmaceutical composition for the treatment of overweight or obesity.

In another aspect, the invention provides the use of a compound of this invention for the preparation of a pharmaceutical composition for the suppression of appetite or for satiety induction.

In another aspect, the invention provides the use of a compound of this invention for the preparation of a pharmaceutical composition for the prevention and/or treatment of disorders and diseases related to overweight or obesity, such as dyslipidaemia, coronary heart disease, gallbladder disease, osteoarthritis and various types of cancer such as endometrial, breast, prostate and colon cancers.

In another aspect, the invention provides the use of a compound of this invention for the preparation of a pharmaceutical composition for the prevention and/or treatment of eating disorders, such as bulimia or binge eating.

In another aspect, the invention provides the use of a compound of this invention for the preparation of a pharmaceutical composition for the treatment of IGT (Impaired glucose tolerance).

In another aspect, the invention provides the use of a compound of this invention for the preparation of a pharmaceutical composition for the treatment of type 2 diabetes.

In another aspect, the invention provides the use of a compound of this invention for the preparation of a pharmaceutical composition for the delaying or prevention of the progression from IGT to type 2 diabetes.

In another aspect, the invention provides the use of a compound of this invention for the preparation of a pharmaceutical composition for the delaying or prevention of the progression from non-insulin requiring type 2 diabetes to insulin requiring type 2 diabetes.

In another aspect, the invention provides the use of a compound of this invention for the preparation of a pharmaceutical composition for the treatment of diseases and disorders in which a stimulation of the H3 histamine receptor has a beneficial effect.

In another aspect, the invention provides the use of a compound of this invention for the preparation of a pharmaceutical composition having histamine H3 agonistic activity.

In another aspect, the invention provides the use of a compound of this invention for the preparation of a pharmaceutical composition for the treatment of allergic rhinitis, ulcer or anorexia.

In another aspect, the invention provides the use of a compound of this invention for the preparation of a pharmaceutical composition for the treatment of Alzheimer's disease, narcolepsy, attention deficit disorders or reduced wakefulness, or for the regulation of sleep.

In another aspect, the invention relates to the use of a compound of this invention for the preparation of a pharmaceutical preparation for the treatment of airway disorders, such as asthma, for regulation of gastric acid secretion, or for treatment of diarrhoea.

In another aspect, the invention provides a method for the treatment of disorders or diseases related to the H3 histamine receptor, the method comprising administering to a subject in need thereof an effective amount of a compound of the general formula I, or of a pharmaceutical composition comprising such a compound.

In another aspect, the invention provides a method as described above, wherein the effective amount of the compound of the general formula I is in the range of from about 0.05 mg to about 2000 mg, preferably from about 0.1 mg to about 1000 mg, and more preferably from about 0.5 mg to about 500 mg per day.

In one aspect, the invention relates to compounds which exhibit histamine H3 receptor antagonistic activity or inverse agonistic activity and which may accordingly be useful in the treatment of a wide range of conditions and disorders in which histamine H3 receptor blockade is beneficial.

In another aspect, the invention provides a method for reduction of weight, the method comprising administering to a subject in need thereof an effective amount of a compound of this invention.

In another aspect, the invention provides a method for treatment of overweight or obesity, the method comprising administering to a subject in need thereof an effective amount of a compound of this invention.

In another aspect, the invention provides a method for suppression of appetite or for satiety induction, the method comprising administering to a subject in need thereof an effective amount of a compound of this invention.

In another aspect, the invention provides a method for prevention and/or treatment of disorders or diseases related to overweight or obesity, such as dyslipidaemia, coronary heart disease, gallbladder disease, osteoarthritis and various types of cancer, for example, endometrial, breast, prostate or colon cancer, the method comprising administering to a subject in need thereof an effective amount of a compound of this invention.

In another aspect, the invention provides a method for prevention and/or treatment of eating disorders, such as bulimia and binge eating, the method comprising administering to a subject in need thereof an effective amount of a compound of this invention.

In another aspect, the invention provides a method for treatment of IGT (Impaired glucose tolerance), the method comprising administering to a subject in need thereof an effective amount of a compound of this invention.

In another aspect, the invention provides a method for the treatment of type 2 diabetes, the method comprising administering to a subject in need thereof an effective amount of a compound of this invention.

In another aspect, the invention provides a method for the delaying or prevention of the progression from IGT to type 2 diabetes, the method comprising administering to a subject in need thereof an effective amount of a compound of this invention.

In another aspect, the invention provides a method for the delaying or prevention of the progression from non-insulin requiring type 2 diabetes to insulin requiring type 2 diabetes, the method comprising administering to a subject in need thereof an effective amount of a compound of this invention.

In another aspect, the invention relates to compounds which exhibit histamine H3 receptor agonistic activity and which may accordingly be useful in the treatment of a wide range of conditions and disorders in which histamine H3 receptor activation is beneficial.

Compounds of this invention may also be used for the treatment of airway disorders (such as asthma), as anti-diarrhoeals, and for the modulation of gastric acid secretion.

Furthermore, compounds of this invention may be used for the treatment of diseases associated with the regulation of sleep and wakefulness, and for the treatment of narcolepsy and attention deficit disorders.

Moreover, the compounds of this invention may be used as CNS stimulants or as sedatives.

The compounds of this invention may also be used for the treatment of conditions associated with epilepsy. Additionally, the compounds of this invention may be used for the treatment of motion sickness and vertigo. Furthermore, they may be useful as regulators of hypothalamo-hypophyseal secretion, as antidepressants, as modulators of cerebral circulation, and in the treatment of irritable bowel syndrome.

Further, compounds of this invention may be used for the treatment of dementia and Alzheimer's disease.

Compounds of this invention may also be useful for the treatment of allergic rhinitis, ulcer or anorexia.

Compounds of this invention may furthermore be useful for the treatment of migraine [see, for example, McLeod et al., *The Journal of Pharmacology and Experimental Therapeutics* 287 (1998), 43-50] and for the treatment of myocardial infarction [see Mackins et al., *Expert Opinion on Investigational Drugs* 9 (2000), 2537-2542].

In a further aspect of the invention, treatment of a patient with a compound of the present invention is combined with diet and/or exercise.

In a further aspect of the invention, one of more compounds of this invention is/are administered in combination with one or more further active substances in any suitable ratio(s). Such further active agents may, for example, be selected from antiobesity agents, antidiabetics, antidyslipidemic agents, antihypertensive agents, agents for the treatment of complications resulting from or associated with diabetes, and agents for the treatment of complications and disorders resulting from or associated with obesity.

Thus, in a further aspect of the invention one or more compounds of this invention may be administered in combination with one or more antiobesity agents or appetite regulating agents. Such agents may, for example, be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TRβ agonists, AGRP (Agouti related protein) inhibitors, opioid antagonists (such as naltrexone), exendin-4, GLP-1 and ciliary neurotrophic factor.

In one embodiment of the invention, an antiobesity agent administered in combination with one or more the compounds of this invention is leptin.

In another embodiment, such an antiobesity agent is dex-amphetamine or amphetamine.

In another embodiment, such an antiobesity agent is fenfluramine or dexfenfluramine.

In still another embodiment, such an antiobesity agent is sibutramine.

In a further embodiment, such an antiobesity agent is orlistat.

In another embodiment, such an antiobesity agent is mazindol or phentermine.

In still another embodiment, such an antiobesity agent is phendimetrazine, diethylpropion, fluoxetine, bupropion, topiramate or ecopipam.

In yet a further aspect of the invention, one or more compounds of this invention may be administered in combination with one or more antidiabetic agents. Relevant antidiabetic agents include insulin, insulin analogues and derivatives such as those disclosed in EP 0 792 290 (Novo Nordisk A/S), for example, $N^{\epsilon B29}$-tetradecanoyl des (B30) human insulin, EP 0 214 826 and EP 0 705 275 (Novo Nordisk A/S), for example, $Asp^{B28}$ human insulin, U.S. Pat. No. 5,504,188, for example, $Lys^{B28}$ $Pro^{B29}$ human insulin, EP 0 368 187, for example, Lantus®, all of which are incorporated herein by reference, GLP-1 derivatives, such as those disclosed in WO 98/08871 (Novo Nordisk A/S), incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells, for example, potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists, such as one of those disclosed in WO 99/01423 and WO 00/39088 (Novo Nordisk A/S), both of which are incorporated herein by reference, GLP-1 agonists, such as those disclosed in WO 00/42026 (Novo Nordisk A/S), incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, one or more compounds of this invention may be administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention, one or more compounds of this invention may be administered in combination with a sulfonylurea, for example, tolbutamide, chlorpropamide, tolaz-amide, glibenclamide, glipizide, glimepiride, glicazide or glyburide.

In another embodiment of the invention, one or more compounds of this invention may be administered in combination with a biguanide, for example, metformin.

In yet another embodiment of the invention, one or more compounds of this invention may be administered in combination with a meglitinide, for example, repaglinide or nateglinide.

In still another embodiment of the invention, one or more compounds of this invention may be administered in combination with a thiazolidinedione insulin sensitizer, for example, troglitazone, ciglitazone, pioglitazone, rosiglitazone, isaglitazone, darglitazone, englitazone, CS-011/CI-1037 or T 174, or a compound disclosed in WO 97/41097, WO 97/41119, WO 97/41120, WO 00/41121 and WO 98/45292, all of which are incorporated herein by reference.

In still another embodiment of the invention, one or more compounds of this invention may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516, or a compound disclosed in WO 99/19313, WO 00/50414, WO 00/63191, WO 00/63192 or WO 00/63193 or in WO 00/23425, WO 00/23415, WO 00/23451, WO 00/23445, WO 00/23417, WO 00/23416, WO 00/63153, WO 00/63196, WO 00/63209, WO 00/63190 or WO 00/63189 (Novo Nordisk A/S), all of which are incorporated herein by reference.

In a further embodiment of the invention, one or more compounds of this invention may be administered in combination with an α-glucosidase inhibitor, for example, voglibose, emiglitate, miglitol or acarbose.

In another embodiment of the invention, one or more compounds of this invention may be administered in combination with an agent acting on the ATP-dependent potassium channel of the β-cells, for example, tolbutamide, glibenclamide, glipizide, glicazide, BTS-67582 or repaglinide.

In yet another embodiment of the invention, one or more compounds of this invention may be administered in combination with nateglinide.

In still another embodiment, one or more compounds of this invention may be administered in combination with an antihyperlipidemic agent or antilipidemic agent, for example, cholestyramine, colestipol, clofibrate, gemfibrozil, lovastatin, pravastatin, simvastatin, probucol or dextrothyroxine.

In still another embodiment of the invention, one or more compounds of this invention may be administered in combination with an antilipidemic agent, for example, cholestyramine, colestipol, clofibrate, gemfibrozil, lovastatin, pravastatin, simvastatin, probucol or dextrothyroxine.

In another aspect of the invention, one or more compounds of this invention may be administered in combination with more than one of the above-mentioned compounds, for example, in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, one or more compounds of this invention may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of compounds according to the invention with diet and/or exercise, one or more of the above-mentioned compounds and optionally one or more other active substances are considered to be within the scope of the present invention.

The present invention also encompasses pharmaceutically acceptable salts of the compounds of this invention. Such salts include pharmaceutically acceptable acid addition salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Also intended as pharmaceutically acceptable acid addition salts are the hydrates which the compound of formula I is able to form.

The acid addition salts may be obtained as the direct products of compound synthesis. Alternatively, the free base may be dissolved in a suitable solvent containing the appropriate acid, and the salt isolated by evaporating the solvent or otherwise separating the salt and solvent.

The compound of formula I may form solvates with standard low molecular weight solvents using methods well known to the person skilled in the art. Such solvates are also to be understood as being within the scope of the present invention.

The invention also encompasses prodrugs of the compounds of this invention which following administration undergo chemical conversion by metabolic processes before becoming active pharmacological substances. In general, such prodrugs will be functional derivatives of the compounds of this invention which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the compounds of this invention.

PHARMACEUTICAL COMPOSITIONS

The compounds of this invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques, such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route, such as the oral, rectal, nasal, pulmonary, topical (including buccal and sublingual), transdermal, intracisternal, intraperitoneal, vaginal or parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also to be understood as being within the scope of the present invention.

Other suitable administration forms include suppositories, sprays, ointments, cremes, gels, inhalants, dermal patches, implants etc.

A typical oral dosage of a compound claimed herein is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses, such as from 1 to 3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be presented in unit dosage form by methods known to those skilled in the art. A typical unit dosage form for oral administration one or more times per day, such as from 1 to 3 times per day, may contain from 0.05 to about 1000 mg, preferably from about 0.1 to about 500 mg, and more preferably from about 0.5 mg to about 200 mg of a compound claimed herein.

For parenteral routes, such as intravenous, intrathecal, intramuscular and similar administration, typical doses are of the order of about half the dose employed for oral administration.

The compounds of this invention are generally utilized as the free substance or as a pharmaceutically acceptable salt thereof. One example is an acid addition salt of a compound having a free base functionality. When a compound of the formula I contains a free base functionality, such salts are prepared in a conventional manner by treating a solution or suspension of the free base form of the compound of formula I with a chemical equivalent (acid-base equivalent) of a pharmaceutically acceptable acid. Representative examples of relevant inorganic and organic acids are mentioned above. Physiologically acceptable salts of a compound of the invention having a hydroxy group include the anion of said compound in combination with a suitable cation, such as sodium or ammonium ion.

For parenteral administration, solutions of the compounds of this invention in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylenes or water. Similarly, the carrier or diluent may include any sustained release material known in the art, such as glyceryl monostearate or glyceryl distearate, alone or mixed with a wax. The pharmaceutical compositions formed by combining the novel compounds of this invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier may vary widely, but will usually be from about 25 mg to about 1 g. If a liquid carrier is used, the preparation may be in the form of a syrup, emulsion, soft gelatine capsule or sterile injectable liquid, such as an aqueous or non-aqueous liquid suspension or solution.

A typical tablet, which may be prepared by conventional tabletting techniques, may in the core contain 5.0 mg of a compound of the invention, 67.8 mg of lactosum Ph. Eur., 31.4 mg of cellulose, microcrystalline (Avicel), 1.0 mg of Amberlite®IRP88 (i.e., Polacrillin potassium NF, tablet disintegrant, Rohm and Haas) and magnesii stearas Ph. Eur. q.s. with a coating of approximately 9 mg of hydroxypropyl methylcellulose and approximately 0.9 mg of Mywacett 9-40 T (being acylated monoglyceride used as plasticizer for film coating).

If desired, the pharmaceutical composition of this invention may comprise the compound of the formula I in combination with one or more further pharmacologically active substances, for example, substances chosen among those described in the foregoing.

Briefly, the compounds of this invention can be prepared in a manner known per se or analogous with known processes.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (for example, "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

The following example is offered by way of illustration, not by limitation.

Example 1

6-(4-Cyclopropylpiperazin-1-yl)-2'-methyl-[3,4'] bipyridinyl, 3 HCl

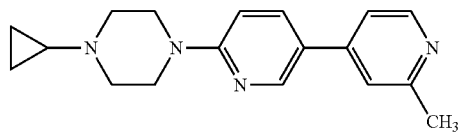

1-(5-Bromopyridin-2-yl)-4-cyclopropylpiperazine (0.3 g, 1.06 mmol), 2-methylpyridine-4-boronic acid (0.16 g; 1.17 mmol) and triphenylphosphinpalladium(II)dichloride (37 mg) were mixed under $N_2$ in a 5 ml microwave vial in acetonitrile (2.5 ml) and 1N sodium carbonate ($Na_2CO_3$; 2.5 ml). The reaction mixture was heated for 500 seconds at 130° C. The reaction mixture was seperated in two phases. The acetonitrile phase was removed and the water phase was extracted with another 2.5 ml of acetonitrile. The combined acetonitrile phases were evaporated in vacuo, redissolved in methanol (MeOH) and purified on a Gilson preparative HPLC (HPLC Method B). (HPLC_E9.S.02_LSk1) The RP-purification was performed on a Gilson system (3 Gilson 306 pumps, Gilson 170 DAD detector and a Gilson 215 liquid handler) using a Waters XTerra® Prep RP$_{18}$ (10 μm, 30 mm×150 mm) with gradient elution, 5% to 95% solvent B (acetonitrile) in solvent A (0.05% trifluoroacetic acid (hereinafter designated TFA) in water) within 15 minutes, 40 mL/min, detection at 210 nm, room temperature.

The title compound was isolated as the TFA salt. The TFA salt was dissolved in MeOH and hydrochlorid acid (HCl) in diethylether was added. Evaporation in vacuo gave the title compound as the trihydrochloride (145 mg, Yield: 34%).

$^1$H-NMR (400 MHz): (DMSO-d$_6$) δ=8.95 (d, 1H), 8.7 (d, 1H), 8.45 (m, 3H), 8.2 (d, d, 1H), 4.6 (d, 2H), 3.5 (m, 4H), 3.25 (m, 2H), 2.85 (m, 1H), 2.7 (s, 3H), 1.2 (m, 2H), 0.8 (m, 2H).

HPLC-MS (electrospray): m/z: 295 M+1=296 Rt=0.58 min.

Elementary analyses gave the following result:
52.8%; C, 6.7%; H, 12.7%; N, 25.3%; Cl.

hERG Binding Assay

The ability of test compounds to bind to the hERG channel was assessed by [3H]Astemizole binding to hERG transfected HEK293 cell membranes essentially as described by PJS Chiu et al. (J Pharmacol Sci 95, 311-319 (2004)). All binding assays were performed in a total volume of 100 μl: 60 μl buffer (10 mM Hepes (pH 7.4), 5 mM KCl, 130 mM NaCl, 0.8 mM MgCl$_2$, 1 mM EGTA, 10 mM glucose and 0.01% BSA) containing 10 μg membrane, 20 μl test drug or vehicle (in buffer containing 5% DMSO) and 20 μl [3H]Astemizole (15 nM in buffer). Non specific binding (NSB) was defined by 10 μM Astemizole (FAC). Incubation was conducted in 96-well polypropylene plates at 25° C. for 60 minutes. Binding was terminated by rapid filtration using a FilterMate Harvester (Packard) onto GF/B filters, presoaked with 0.3% polyethyleneimine, followed by rapid washing with 10×300 μl ice cold washing buffer (25 mM Tris (pH 7.4), 5 mM KCl, 130 mM NaCl, 0.8 mM MgCl$_2$, 0.05 mM CaCl$_2$, and 0.01% BSA). After drying of plates and addition of 50 μl MicroScint 0 (Perkin Elmer), captured radiolabel was detected using a Perkin Elmer TopCount NXT. Results are presented as percent inhibition of [3H]Astemizole binding at a given concentration of test compound (typically 10 μM).

What is claimed is:

1. A compound of Formula (I)

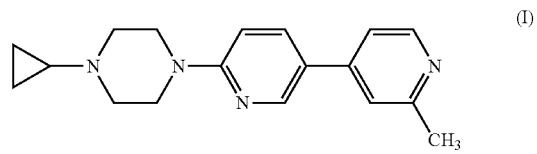

or a pharmaceutically acceptable salt thereof.

2. The compound of claim 1, where the compound is in the form of a hydrochloride salt.

3. The compound of claim 2, where the compound is in the form of a trihydrochloride salt.

4. The compound of claim 1, where the compound is in the form of a trifluoroacetate salt.

5. The compound of claim 4, where the compound is in the form of a mono-trifluoroacetate salt.

6. A pharmaceutical composition comprising: a compound of Formula (I)

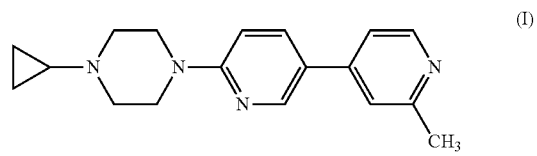

or a pharmaceutically acceptable salt thereof; and a pharmaceutically acceptable carrier or diluent.

7. The pharmaceutical composition of claim 6, where the compound is in the form of a hydrochloride salt.

8. The pharmaceutical composition of claim 7, where the compound is in the form of a trihydrochloride salt.

9. The pharmaceutical composition of claim 6, where the compound is in the form of a trifluoroacetate salt.

10. The pharmaceutical composition of claim 9, where the compound is in the form of a mono-trifluoroacetate salt.

* * * * *

UNITED STATES PATENT AND TRADEMARK OFFICE
CERTIFICATE OF CORRECTION

PATENT NO.        : 8,318,927 B2  
APPLICATION NO.   : 12/301919  
DATED             : November 27, 2012  
INVENTOR(S)       : Lundbeck et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 549 days.

Signed and Sealed this  
Thirteenth Day of August, 2013

Teresa Stanek Rea  
*Acting Director of the United States Patent and Trademark Office*